(12) United States Patent
Goda et al.

(10) Patent No.: US 7,138,241 B2
(45) Date of Patent: Nov. 21, 2006

(54) HYBRIDOMA, AN ANTIBODY RESISTANT TO AN INTERFERING SUBSTANCE, AND A KIT FOR IMMUNOLOGICAL ANALYSIS

(75) Inventors: Yasuhiro Goda, Osaka (JP); Ayako Kobayashi, Osaka (JP); Masato Hirobe, Osaka (JP)

(73) Assignee: Japan Envirochemicals, Ltd., Osaka (JP)

( * ) Notice: Subject to any disclaimer, the term of this patent is extended or adjusted under 35 U.S.C. 154(b) by 662 days.

(21) Appl. No.: 10/146,816

(22) Filed: May 17, 2002

(65) Prior Publication Data

US 2003/0064389 A1 Apr. 3, 2003

(30) Foreign Application Priority Data

May 18, 2001 (JP) ............................. 2001-149832

(51) Int. Cl.
*G01N 33/53* (2006.01)
*C07K 16/00* (2006.01)

(52) U.S. Cl. .................... 435/7.1; 435/70.21; 435/325; 435/451; 435/452; 435/326; 436/501; 436/512; 436/517; 436/547; 424/130.1; 424/178.1; 530/387.1

(58) Field of Classification Search ............... 435/7.1, 435/70.21, 325, 451, 452, 326; 436/501, 436/512, 517, 547; 424/130.1, 178.1; 530/387.1
See application file for complete search history.

(56) References Cited

U.S. PATENT DOCUMENTS 4,444,879 A * 4/1984 Foster et al. ............... 435/7.95

OTHER PUBLICATIONS

Mandal et al. (Steroids, 52 (5-6), 1998 pp. 551-560).*
Rao et al. (Clinical Chemistry, vol. 36, No. 6, 1990 p. 1099-1100, 0691).*
Kundu (Steroids, 22:3, Sep. 1973, pp. 327-336).*
J. P. Aston et al., "Water Immiscible Solvent Based Immunoassay", Journal of Immunoassay, vol. 18, No. 3, pp. 235-246, 1997.
A. J. Russell et al., "Antibody-Antigen Binding in Organic Solvents", Biochemical and Biophysical Research Communications, vol. 158, No. 1, pp. 80-85, Jan. 16, 1989.

* cited by examiner

*Primary Examiner*—Long V. Le
*Assistant Examiner*—Lisa V. Cook
(74) *Attorney, Agent, or Firm*—Wenderoth, Lind & Ponack, L.L.P.

(57) ABSTRACT

The present invention provides for a method of selecting an antibody against a target substance to be measured, which comprises selecting the antibody against the target substance by antigen-antibody reaction in the presence of a substance interfering with the antigen-antibody reaction. That is, an antigen and a labeled antigen are reacted with the antibody in the presence of an interfering substance, such as an environment pollutant, and on the basis of the degree of reaction thereof, the antibody against the target substance, which is highly resistant to the interfering substance, is selected. Thereby, even if a test sample is contaminated with a substance interfering with antigen-antibody reaction, the antibody, which is highly resistant to the substance interfering with antigen-antibody reaction, is not influenced by the interfering substance and gives a correct value in the quantification. The present invention further provides for antibodies, which are highly resistant to the substance interfering with the antigen-antibody reaction, and hybridomas producing the antibodies.

4 Claims, 1 Drawing Sheet

[Fig. 1]
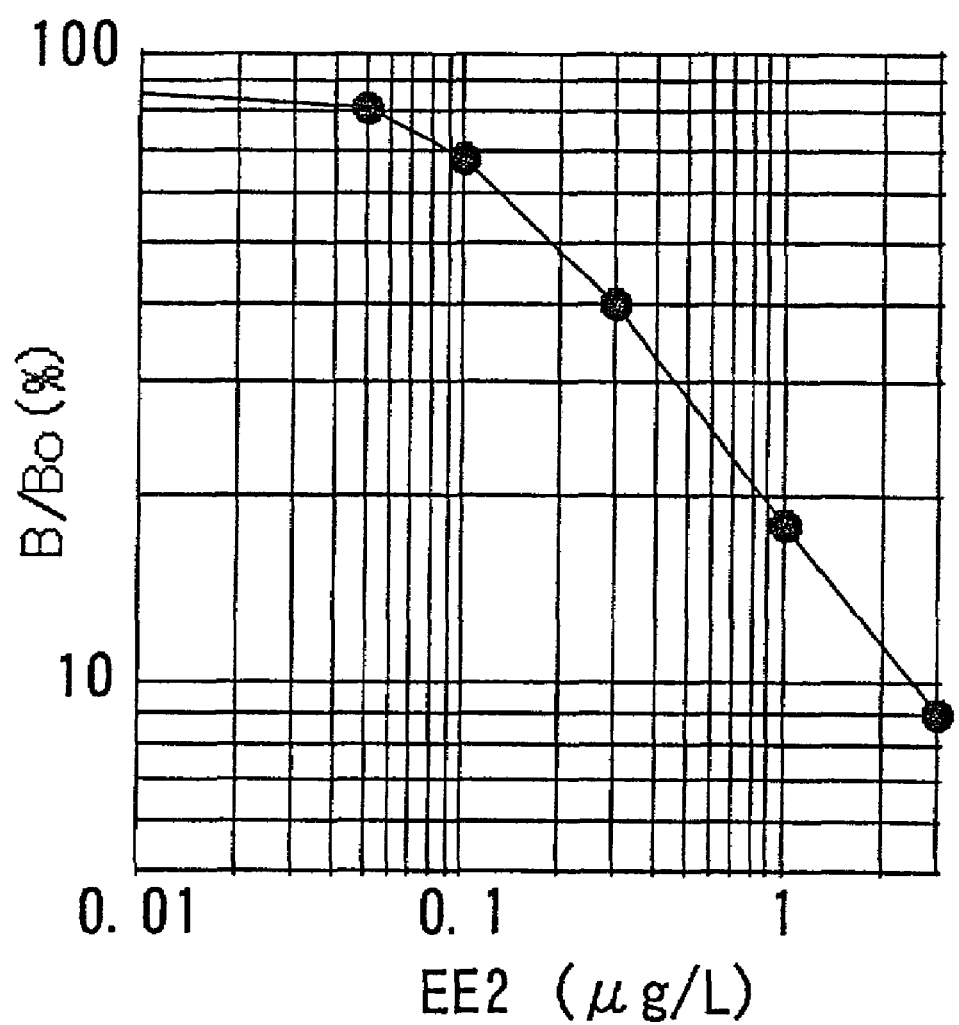

HYBRIDOMA, AN ANTIBODY RESISTANT TO AN INTERFERING SUBSTANCE, AND A KIT FOR IMMUNOLOGICAL ANALYSIS

FIELD OF THE INVENTION

This invention relates to an antibody having a property of reacting with an antigen while being hardly influenced even in the presence of an substance interfering with antigen-antibody reaction (hereinafter also called an interfering substance), that is, an antibody resistant to or tolerant of an interfering substance, a method of selecting the antibody, a hybridoma producing the antibody, and use of the antibody.

BACKGROUND OF THE INVENTION

In recent years, in the fields of environmental quantification etc., immunoassays (hereinafter abbreviated to IA) are frequently used because expensive devices and proficiency in the operation are not necessary.

However, the antibody used in IA, which acts specifically on a target substance to be measured, is a high-molecular protein, and thus the activity of the antibody is influenced by various substances exerting an influence on the protein, and as a result, quantifications are inaccurate in some cases.

On one hand, prior to measurement of a target substance existing in a very small amount in the order of ppb (part per billion) and ppt (part per trillion), concentrating the sample at high degrees may be necessary, and in such cases, the sample concentrated by a solid-phase extraction method (hereinafter also called solid-phase concentration) or by extraction with a solvent (hereinafter also called solvent concentration) is used to measure the target substance.

However, the test sample contains a wide variety of compounds in addition to the target substance, and thus when the test sample is concentrated by solid-phase concentration or solvent concentration, a compound exerting an influence on the antibody, that is, a substance interfering with the antigen-antibody reaction is also concentrated, and as a result, the activity of the antibody is influenced, resulting in abnormal values of quantifications in some cases.

One object of this invention is to provide a method of selecting an antibody which in measurement of the antigen by IA, is hardly influenced by an interfering substance with which a sample may possibly be contaminated, whereby occurrence of incorrect measurement in IA is prevented.

Another problem of this invention is to provide an IA kit with little occurrence of incorrect values by utilizing an antibody tolerant of or resistant to a substance interfering with the antigen-antibody reaction.

SUMMARY OF THE INVENTION

The present inventors made extensive study for establishing a method of detecting and measuring various substances by IA with minimum influence of contaminated interfering substances. As a result, the present inventors found that, for selection of an antibody used in IA, an antigen and a labeled antigen are reacted with the antibody in the presence of an interfering substance such as an environment pollutant, a decomposed product thereof, a germicidal disinfectant or a solvent, and on the basis of the degree of reaction thereof, the antibody against the target substance highly resistant to the interfering substance is selected, thereby making it possible to detect and measure a sample even concentrated at a high degree because of a small amount of a target substance to be measured. As a result of further extensive study on the basis of such finding, the present inventors have completed the invention.

That is, this invention provides:

(1) A method of selecting an antibody against a target substance to be measured which comprises selecting the antibody against the target substance by antigen-antibody reaction in the presence of a substance interfering with the antigen-antibody reaction.

(2) The method of selecting an antibody according to (1), wherein the target substance to be measured is an environmental pollutant.

(3) The method of selecting an antibody according to (1), wherein the target substance to be measured is a hormone.

(4) The method of selecting an antibody according to (1), wherein the antibody against the target substance is a monoclonal antibody.

(5) The method of selecting an antibody according to (1), wherein the substance interfering with the antigen-antibody reaction is an environmental pollutant, a decomposed product thereof, a germicidal disinfectant or a solvent.

(6) The method of selecting an antibody according to (5), wherein the environmental pollutant as a substance interfering with the antigen-antibody reaction is a surfactant, environment water, a concentrate thereof or a humic substance.

(7) The method of selecting an antibody according to (6), wherein the surfactant is an anionic surfactant, a cationic surfactant or a nonionic surfactant.

(8) The method of selecting an antibody according to (6), wherein the environment water or a concentrate thereof is river water, lake water, seawater, water in a tap water-treatment process, water in a waste water treatment process or a concentrate thereof.

(9) The method of selecting an antibody according to (5), wherein the germicidal disinfectant is a chlorine agent.

(10) The method of selecting an antibody according to (5), wherein the solvent is an alcohol, nitrile, ketone or ester.

(11) The method of selecting an antibody according to (1), wherein a polyclonal antibody [obtained from an animal immunized with a target substance to be measured or a conjugate between a hapten of the target substance to be measured and a carrier protein as the antigen, or a monoclonal antibody obtained by culturing a hybridoma producing a monoclonal antibody against a target substance to be measured or a conjugate between a hapten of the target substance to be measured and a protein, and being obtained by fusing myeloma cells and spleen cells or lymph node cells from an animal immunized with the target substance to be measured or a conjugate between a hapten of the target substance to be measured and a carrier protein as the antigen, is reacted with an antigen-enzyme conjugate (labeled antigen), the target substance to be measured or a conjugate between a hapten of the target substance to be measured and a carrier protein (antigen) in the presence of an substance interfering with the antigen-antibody reaction, and on the basis of the degree of reaction thereof, an antibody resistant to the substance interfering with the antigen-antibody reaction is selected.

(12) A hybridoma producing the monoclonal antibody resistant to an substance interfering with the antigen-antibody reaction, which was selected according to the method of (11).

(13) The hybridoma according to (12), wherein the hybridoma is mouse hybridoma EE2-227 (FERM BP-7567), mouse hybridoma E1-420 (FERM BP-7568) or mouse hybridoma E2-73 (FERM BP-7569).

(14) An antibody resistant to a substance interfering with the antigen-antibody reaction, which was selected by the method of (11).

(15) A monoclonal antibody resistant to an interfering substance, which was produced by the hybridoma of (12) or (13).

(16) A kit for immunological analysis of a target substance to be measured, which comprises the antibody resistant to a substance interfering with the antigen-antibody reaction of (14) or (15).

(17) A kit for immunological concentration of a target substance to be measured, which comprises the antibody resistant to a substance interfering with the antigen-antibody reaction of (14) or (15).

DETAILED DESCRIPTION OF THE DRAWING

FIG. 1 shows an EE2-227 antibody standard curve.

DETAILED DESCRIPTION OF THE INVENTION

This invention relates to a method of selecting an antibody, wherein a substance interfering with antigen-antibody reaction and an antibody against a target substance to be measured are allowed to coexistent in an aqueous medium, and an antibody resistant to the interfering substance is selected by IA.

The method of selecting an antibody will be concretely described. That is, a solution containing an antibody against a target substance to be measured is contacted as such with the carrier or contacted with a species specific immunoglobulin antibody previously immobilized on the carrier and then reacted for a suitable time at a suitable temperature, whereby the antibody in the antibody-containing solution is immobilized on the carrier. The non-immobilized antibody in the antibody-containing solution is removed by washing with a washing solution, and then a hapten-enzyme conjugate (labeled antigen), a target substance to be measured (antigen) and an interfering substance are contacted and reacted with the immobilized antibody. The unreacted materials are removed by washing, and an enzyme substrate is added for coloration. After coloration or termination of coloration, the absorbance or fluorescence is measured, and using the resultant standard curve, the concentration of the sample measured in the presence of the interfering substance is compared with that in the absence of the interfering substance, and the degree of resistance to the interfering substance is calculated. As a result of this calculation, an antibody, which is highly resistant to the interfering substance, is selected. When the antibody is a monoclonal antibody, a hybridoma producing the monoclonal antibody is selected. The hybridoma is cultured, and from the culture supernatant, a monoclonal antibody, which highly resistant to the interfering substance, is obtained. By using these antibodies, the target substance to be measured is analyzed by IA.

The antibody selected by the method of this invention includes any antibodies used in detection and quantification. The antibodies include polyclonal antibodies and monoclonal antibodies.

The target substance to be measured by this invention includes every substance to be detected and measured by using the antibody, and includes every substance to be quantified, e.g. an environmental pollutant. Examples of the substance to be measured include various hormones, plant hormones, environmental pollutants, synthetic surfactants, agrochemicals, fungal toxins, toxins, chemicals, allergens, microorganisms and the like.

Among various hormones, animal hormones are exemplified by female hormones such as estrogen, estradiol (E2), estrone (E1), estriol (E3) etc., male hormones such as androgen, testosterone, dehydroandrosterone, androstanedione etc., thyroid hormones such as thyroxin (T3), triiodothyronine (T4) etc., synthetic hormones such as ethynylestradiol, diethylstilbestrol, raloxifene, tamoxifen, moxestrol, allylestrenol, mestranol, lynestrenol, chlormadinone acetate, dydrogesterone, medroxyprogesterone, norethisterone, norgestrel, levonorgestrel, pregnandiol, clomiphene etc., and hormones such as progesterone, zeranol, trenboron, clenbuterol (β-agonist) etc. Further, the substance to be measured includes conjugated metabolites thereof (e.g., conjugated glucuronic acid, conjugated sulfuric acid etc.) and decomposed products thereof.

The plant hormones include isoliquiritigenin, phloretin, coumestrol, hesperetin, naringenin, apigenin, baicalein, chrysin, luteolin, galangin, kaempferol, quercetin, equol, biochanin A, daidzein, formononetin, genistein, betulin etc., as well as metabolites and decomposed products thereof.

As the substance to be measured, the environmental pollutant includes ester phthalates such as benzylbutyl phthalate, diethyl phthalate, di-n-butyl phthalate, diisobutyl phthalate, di-n-propyl phthalate, di-n-pentyl phthalate, di-n-hexyl phthalate, dicyclohexyl phthalate, di(2-ethylhexyl) phthalate, dioctyl phthalate, mono(2-ethylhexyl) phthalate, diisononyl phthalate, diisodecyl phthalate, di-n-octyl phthalate, ditridecyl phthalate etc., ester adipates such as di(2-ethylhexyl) adipate etc., alkyl phenols such as 4-ethyl phenol, 3-t-butyl phenol, 4-s-butyl phenol, 4-t-butyl phenol, 4-propyl phenol, 4-isopentyl phenol, 4-t-pentyl phenol, octyl phenol, 4-octyl phenol, 4-t-octyl phenol (4-1,3,3-tetramethylbutylphenol), 4-nonyl phenol (linear), 4-nonyl phenol (branched), nonyl phenol (mixture of isomers) etc., diphenyl alkanes such as bisphenol A, tetrabromobisphenol A etc., PBBs such as poly(biphenyl bromide), poly(biphenylether bromide), styrene, styrene dimer, styrene trimer, chlorophenols such as 2-chlorophenol, 2,4-dichlorophenol, 2,4,6-trichlorophenol, pentachlorophenol etc., and endocrine disrupting chemicals such as t-butyl hydroxyanisole (BHA), n-butyl benzene, benzophenone, 6-bromo-2-naphthol, dibromoacetic acid, 2-bromopropane, 4-nitrotoluene, octachlorostyrene etc., as well as metabolites and decomposed products thereof Further, the substance to be measured includes dioxins (polychlorinated dibenzodioxins (PCDDs)) such as 2,3,7,8-tetrachlorodioxins (2,3,7,8-TCDD), dibenzofurans (polychlorinated dibenzofurans (PCDFs)) such as 2,3,7,8-tetrachlorodibenzofuran (2,3,7,8-TCDF), PCBs (polychlorinated biphenyls) such as Aroclor 1016, Aroclor 1221, Aroclor 1232, Aroclor 1242, Aroclor 1248, Aroclor 1254, Aroclor 1260, Aroclor 1262, Aroclor 1268, Bifenox, Halowax 1000, Halowax 1051, Halowax 1099 etc., polynuclear aromatic hydrocarbons (PAHs), cyclic polynuclear aromatic hydrocarbons (C-PAHs) and total petroleum hydrocarbons (TPHs)), such as acenaphtene, acenaphthylene, anthracene, benzo[a]anthracene, benzo[a]pyrene, benzo[b]fluoranthene, benzo[g.h.i]perylene, benzo[k]fluoranthene, biphenyl, chrysene, creosote, 1,2-dichlorobenzene, 2-ethyltoluene, 4-ethyltoluene, hexachlorobenzene, dibenzo[a,h]anthracene, fluoranthene, fluorene, naphthalene, 1-methyl-naphthalene, 2-methyl-naphthalene, 1-chloro-naphthalene, o-cresol, phenanthrene, n-propylbenzene, pyrene, 1,2,4-trimethylbenzene, 1,3,5-trimethylbenzene, gasoline, kerosene, jet A fuel, JP-4, JP-5, fuel oil #1, fuel oil #2, fuel oil #4, fuel oil #6, heating fuel, diesel fuel, turbine fuel etc., BTEX (benzene, toluene, ethyl benzene, and xylene), benzene, 2-amino-4,6-dinitrotoluene, 4-amino-2,6-dinitrotoluene, 2,4-dinitroaniline, 1,3-dinitrobenzene, 2,4-dinitrophenol, 2-nitrotoluene, 3-nitrotoluene, 2,4-dinitrotoluene, 2,6-dinitrotoluene, picric acid, methyl-2,4,6-trinitrophenylnitramine, 1,3,5-trinitrobenzene, trinitrotoluene (TNT), octahydro-1,3,5,7-tetranitro-1,3,5,7-tetrazocine, nitroglycerine, nitroguanidine, pentaerythritol tetranitrate, RDX explosives, gold trichloride, silver nitrate, mercury, trihalomethanes (THMs), trichloroethylene (TCE), tetrachloroethylene (TCE) etc.

The synthetic surfactant includes e.g. anionic surfactants such as linear alkylbenzene sulfonic acids and salts thereof, and nonionic surfactants such as nonylphenol ethoxylate, octylphenol ethoxylate etc., as well as metabolites and decomposed products thereof.

The agrochemicals include carpropamide, thiocarbamate type compounds, chlorphenapyl, pretilachlor, propyzamide, chloromecote, malathion, phenytrothion, imidachropride, carbaryl, inabenfide, butamifos, probenazol, isoprothiolan, bentazone, torchlorofos methyl, phensulphothion, bendiocarb, iprodione, isoxathion, pirimicarb, oxamyl, daminozide, phoxim, imazalyl, microtutanyl, triflumizole, diazinon, propiconazole, viteltanol, phenoxyacetate, acid amide type compounds, 2,4-D, 2,4-DNT, 2,4-D butyric butyl ester, acetanilide, acetochlor, alachlor, alachlor sulfonic acid, aldicarb, aldicarb sulfone, aldicarb sulfoxide, aldrin, ametryn, atrazine, azinphos, benomyl, BHC-alpha, BHC-delta, BHC-gamma (lindane), bioresmethrin, captan, carbaryl, carbendazim, carbofuran, chlordane, chlorothalonil, chlorpyrifos, chlorpyrifos methyl, chlorosulfuron, cyanazine, cyclodienes, DDD, DDE, DDT, dicamba, dichlorprop, dieldrin, diquat, dursban, endosulfan, endrin, ethylated atrazines, fenitrothion, heptachlor, hexazinone, hydroxy atrazine, imazaquin, imazapyr, isoproturon, metsulfuron, metalaxyl, methomyl, methoprene, metolachlor, metribuzin, molinate, paraquat, parathion, picloram, pirimiphos-methyl, procymidone, prometon, prometryn, reldan, silvex, silvex 2,4,5-TP, simazene, thiabendazole, toxaphene, triasulfuron, triazine, trichloropyridinol, trichlopyr, trifluralin, and urea herbicides, as well as metabolites and decomposed products thereof.

The fungal toxins include aflatoxin, T2 toxin, ochratoxin, zearalenone, DON (deoxynivalenol, vomitoxin), fumonisin etc. and metabolites and decomposed products thereof.

The toxin includes paralytic shellfish toxins, yellow staphylococcal enterotoxins (A, B, C, D, E) and metabolites and decomposed products thereof.

The chemicals include β-lactam antibiotics containing a skeleton such as penicillin, cephalosporin, penem, monobactam or clavuric acid, polyether antibiotics such as monensin, salinomycin, enduracidin etc., aminoglucoside antibiotics such as kanamycin, newquinolone synthetic antimicrobial agents such as enrophroxane, sulfur drugs such as sulfamethazine, sulfadimethoxin etc., antibiotics such as chloramphenicol, gentamicin etc., chemicals such as digoxin, theophylline, phenobarbital, trenboron etc., as well as metabolites and decomposed products thereof.

The allergens include house dust, tick, cat epithelium, dog epithelium, cedar, Japanese cypress, alder, *Anthoxanthum odorathum, Dectylis glomereta*, timothy, ragweed, mugwort, *Aspergillus, Candida, Arternalia*, egg white, milk, wheat, rice, soybean, codfish, tuna, crab, lobster, *Penicillium, Chladosporium*, chowder cheese, beef, chicken meat, salmon etc., as well as metabolites and decomposed products thereof.

The microorganisms include pathogenic microorganism such as *Salmonella, Listeria, E. coli, Cryptosporidium Ziardia, Campylobacter*, yellow *Staphylococcus, Yersinia*, enteritis *Vibrio* and fungus, as well as constituent components thereof On one hand, the substance interfering with the antigen-antibody reaction includes substances exerting an influence on the protein such as antibody and enzyme, for example environmental pollutants, decomposed products thereof, germicidal disinfectants, solvents etc.

The environmental pollutants and decomposed products thereof include surfactants, environmental water and concentrates thereof, humic substances etc.

The surfactants are exemplified by anionic surfactants including oils, fats, fatty acids, sulfate esters thereof, sulfate ester type such as alkyl sulfate, alkyl ether sulfate etc., sulfonic acid type such as (alkyl) sulfonate, (alkyl) naphthalenic acid, other sulfonates and phosphate type; cationic surfactants; and nonionic surfactants including ether type such as polyoxyethylene alkyl ether, polyoxyethylene alkyl allyl ether and other ethers, ester ether type such as polyvalent alcohol type ester-ether and other ester ethers, and polyvalent alcohol esters.

The humic substance includes fulvic acid, humic acid, humin and salts thereof

The environmental water and concentrates thereof include river water, lake water, seawater, water in tap water-treatment process, water in waste water treatment process or a concentrate thereof.

The germicidal disinfectants include chlorine agents i.e. chlorine gas and hypochlorous acid and salts thereof.

The solvents include alcohols, nitrites, ketones, esters etc., and the alcohols include methanol, ethanol, propanol, butanol etc., the nitrites include acetonitrile etc., the ketones include acetone, methyl isobutyl ketone (MIBK) etc., and the esters include ethyl acetate etc.

Production of immunoglobulin (Ig) which is an antibody against a target substance to be measured, and production of an antibody to the Ig (that is, anti-Ig antibody), can be conducted by a known method, for example a method described in Enzyme Immunoassay, pp. 46–71 and pp. 85–110 (authored by P. TIJSSEN and translated by Eiji Ishikawa, Tokyo Kagaku Dojin (1989)) or a method analogous thereto.

In these methods, a substance to be measured which can be an immunogen by itself is inoculated as such into an animal, while a substance to be measured which has no immunogenicity is used to prepare a hapten which is then formed into a conjugate (immunogen) with a carrier protein, and inoculated into an animal. The carrier protein for forming the conjugate for immunization includes e.g. bovine serum albumin (abbreviated hereinafter to BSA), ovalbumin (abbreviated hereinafter to OVA), keyhole limpet hemocyanin (abbreviated hereinafter to KLH), bovine thyroglobulin (abbreviated hereinafter to BTG) etc.

Formation of a conjugate between a substance to be measured and a carrier protein can be carried out for example by fusing a compound (hapten) represented by formula (1):

$$A-R \qquad (1)$$

(wherein R represents COOH, $NH_2$ or SH, and A represents a group which upon removal of the R group, becomes a substance to be measured) with a carrier protein in a method known per se.

For example, a compound represented by formula (1) wherein R is COOH, and A is polyoxyethylene alkyl phenyl ether can be produced by dehydration condensation (half esterification) of polyoxyalkyl phenyl ether and succinic anhydride [Cancer Biochemistry Biophysics, 7, 175 (1984)].

A compound represented by formula (1) wherein R is $NH_2$, and A is polyoxyethylene alkyl phenyl ether can be produced by converting a hydroxyl group of polyoxyalkyl phenyl ether into hydrochloric acid with thionyl chloride [Journal of American Chemical Society, 60, 2540 (1938)] followed by treatment with ammonia [Organic Functional Group Preparations, vol. 1, p. 382].

A compound represented by formula (1) wherein R is SH, and A is polyoxyethylene alkyl phenyl ether can be produced by converting a hydroxyl group of polyoxyalkyl phenyl ether into hydrochloric acid with thionyl chloride [Journal of American Chemical Society, 60, 2540 (1938)] followed by treatment with sodium hydroxide [Journal of American Chemical Society, 72, 1843 (1950)].

In this invention, the antibody against a target substance to be measured can be produced in a method known per se, that is, by allowing a polyclonal antibody to be produced by an animal immunized with a substance to be measured or a conjugate (immunogen) between a hapten of the substance to be measured and a carrier protein, or by allowing a monoclonal antibody to be produced by a monoclonal antibody-producing hybridoma obtained by fusing myeloma cells and spleen cells or lymph node cells from the immunized animal.

For immunization of an animal, the substance to be measured or the conjugate between its hapten and a carrier protein obtained above is inoculated into the animal. The animal into which it is inoculated includes e.g. goats, sheep, rabbits, rats, mice, guinea pigs, chickens etc., but when a monoclonal antibody to the substance to be measured is desired, mice are preferably used.

The inoculation method may be a method conventionally carried out, and for example, about 1 to 100 μg, preferably 50 to 100 μg is emulsified with an equal volume (0.1 ml) physiological saline and Freund's complete adjuvant or in RIBI adjuvant system™, and inoculated subcutaneously into the back or abdomen or intraperitoneally 2 to 6 times at 2- to 3-weeks intervals. To obtain the polyclonal antibody, it is collected from serum in the immunized animal. To obtain the monoclonal antibody, the following operation is further conducted.

From these immunized animals such as mice, an individual having a high antibody titer is selected, and 3 to 5 days after final immunization, the spleen or lymph node is collected, and antibody-producing cells contained therein are fused with myeloma cells.

As the method of immunization, the known in vitro immunization method or mouse footpad method can be used to increase the antibody titer in a shorter time.

The operation of fusion can be carried out in a known method, and the fusion promoter such as polyethyleneglycol (abbreviated hereinafter to PEG) or Sendai virus is used, and PEG is preferably used. Fusion can also be carried out by a known method using electric pulses (pulse electric fusion).

As the myeloma cells, NS-1, P3U1, Sp2/O etc. are used, and particularly P3U1 is preferable. For example, the proportion of the spleen cells and myeloma cells is preferably about 1:1 to 10:1, to which PEG having a molecular weight of about 1,000 to 6,000 is added at a concentration of about 10 to 80%, and these cells are then incubated for about 3 to 10 minutes at about 20 to 37° C., preferably 30 to 37° C.

Production of the monoclonal antibody by the hybridoma and purification thereof can also be conducted in a method known per se. The resultant monoclonal antibody serves as an antibody to the substance to be measured or the compound represented by formula (1).

Specifically, methods for producing and purifying an antibody are described, for example, in the above-mentioned "Enzyme Immunoassay", pp. 46–71 and pp. 85–110, and mention is made of methods by salting-out ($Na_2SO_4$, $(NH_4)_2SO_4$), ion exchangers (DEAE (Diethylaminoethyl), QAE (Ouatemary Aminoethyl), CM/cellulose (Carboxymethyl Cellulose), SEPHADEX ((Pharmacia Fine Chemicals, Inc.): dextran gel beads), SEPHAROSE ((Pharmacia Fine Chemicals, Inc.): agarose gel beads), etc.), gel filtration (SEPHADEX G-200, BIO-GEL P-300, etc.), electrophoresis (zone electrophoresis on agarose gel, isoelectric focusing, isotachophoresis, etc.), ultracentrifugation (sucrose density gradient centrifugation), affinity chromatography (immobilized protein A (PROTEIN A SEPHAROSE, PROTEIN A SUPEROSE, etc.), immobilized protein G (PROTEIN-G SEPHAROSE, etc.)), etc.

As the antibody-immobilizing carrier (hereinafter also called a carrier) used in this invention, the one conventionally used in immunoassays can be used. Examples thereof include a microplate (for example, 96-wells microplate, 24-wells microplate, 192-wells microplate, 384-wells microplate, etc.), a test tube (for example, glass test tube, plastic test tube), glass particles, polystyrene particles, modified polystyrene particles, polyvinyl particles, latexes (for example, polystyrene-latex), a nitrocellulose membrane, a cyan bromide-activated filter paper, a DMB-activated filter paper, a granular solid phase (for example, SEPHAROSE ((Pharmacia Fine Chemicals, Inc.): agarose gel beads), SEPHADEX ((Pharmacia Fine Chemicals, Inc.): dextran gel beads), agarose, cellulose, SEPLIACYL ((Pharmacia Fine Chemicals. Inc.): cross-linked copolymer beads of allyl dextran and N,N-methylenebisacrylamide, etc.), an iron-containing polycarbonate membrane, magnet-containing beads, etc.

The antibody can be carried on the carrier by a method known per se [for example, the above-mentioned "Enzyme Immunoassay", pp. 268–296, "Affinity Chromatography Handbook" (Amersham Pharmacia Biotech Co., Ltd.(published on Dec. 20, 1998)] etc.

The antibody-containing solution for screening of the antibody resistant to the interfering substance may use in any stages in the process of screening of the antibody, such as serum from an immunized animal, a culture supernatant on a well confirmed to contain a colony of fused cells (hybridoma) under screening with HAT, a culture supernatant of the hybridoma under cloning, a culture supernatant of a hybridoma made mono-cloned by cloning, an ascites fluid containing mono-cloned hybridomas multiplied in a mouse ascites, or an antibody solution purified from the mouse ascites.

Depending on the concentration of the antibody in the antibody-containing solution, the antibody-containing solution may be diluted before addition. The degree of dilution may be varied depending on the concentration of the antibody and assay conditions, but in some cases, the antibody-containing solution should be diluted to a degree of dilution of several to several hundreds of thousands before quantification.

The antigen-enzyme conjugate (labeled antigen) may have any structure insofar as it reacts with the antibody to be obtained. The enzyme and its substrate may be any ones insofar as they are enzymes and their substrates used in general enzyme immunoassays, for example, alkali phosphatase, alcohol dehydrogenase, β-D-galactosidase, glucose-6-phosphate dehydrogenase, horseradish peroxidase, xanthine oxidase, glucose oxidase, invertase, acetate kinase and substrates thereof are preferable, and horseradish peroxidase and its substrate are preferable in respect of quantification sensitivity.

The concentration of the antigen-enzyme conjugate (labeled antigen) added is previously diluted with a phosphate buffer, physiological saline etc. such that the absorbance of the blank not containing the substance to be measured (antigen) and the interfering substance is 1 to 2.

The substance to be measured is diluted with a buffer or 10% methanol such that the degree of inhibition is about 50% when the interfering substance is not added, and the interfering substance added is diluted stepwise at a final concentration of 1 to 1000 mg/L with a buffer, 10% methanol etc. For an interfering substance in environmental water or a concentrate thereof, the original water or a concentrate thereof is used. Preparation of the concentrate of environmental water may be conducted in any known methods such as solvent concentration, solid phase concentration or concentration by evaporation and drying, and the degree of concentration may be varied depending on the type of environmental water used, but unless the water is solidified to fail to form a solution with a buffer, a solvent or the like, any degrees of dilution may be used. When a solvent is used as the interfering substance, the solvent is added in the range of less than 100%.

The antigen-enzyme conjugate (labeled antigen), the substance to be measured (antigen), and the interfering substance are mixed and then reacted with an immobilized antibody to the substance to be measured or with an antibody against the substance to be measured bound to an immobilized species specific immunoglobulin antibody, and the reaction temperature and reaction time may be under any conditions where the antibody to the substance to be measured or the species specific immunoglobulin antibody is not denatured, but it is usually preferable that the reaction is conducted overnight (16 to 24 times) at 4° C. or for 0.1 to 4 hours at room temperature.

The washing solution for unreacted substances may be any solutions insofar as the antibody is not denatured therein, but phosphate buffered physiological saline (PBS), T-PBS containing Tween 20, etc. are preferable in order to suppress a change in pH.

The enzyme substrate for coloration may be any substrates for the enzyme used. For example, the following substrates are known: for alkali phosphatase in colorimetry, p-nitorphenyl phosphoric acid, phenyl phosphoric acid/4-aminoantipyrine, or in fluorometry, 4-methylumbelliferyl phosphoric acid, o-methylfluorescein acid, flavone-3-diphosphoric acid, or in chemiluminescence, oxidoreductase/ethanol/ADH/NADH, isoluminol/microperoxidase, ascorbic acid-2-phosphoric acid/lucigenin/OH—, BCIP (5-bromo-4-chloro-3-indoxylyl) phosphoric acid/isoluminol/microperoxidase, AMPPD (3-(2'-spiroadamantane)-4-methoxy-(3'-phosphoryloxy) phenyl 1,2-dioxetane), CSPD (3-(2-chlorinated adamantane)-4-methoxy-(3'-phosphoryloxy) phenyl 1,2-dioxetane), or in bioluminescence, D-luciferin phosphoric acid/luciferase; for peroxidase in colorimetry, 5-aminosalicylic acid/hydrogen peroxide, ABTS (2,2'-azinodi(3-ethylbenzthiazoline)-6-sulfonic acid)/hydrogen peroxide, tetramethyl benzidine/hydrogen peroxide, o-phenylene diamine/hydrogen peroxide, or in fluorometry, homovanillic acid/hydrogen peroxide, tyramine/hydrogen peroxide, p-hydroxyphenyl propionic acid/hydrogen peroxide, or in chemiluminescence, luminol/hydrogen peroxide, luminol/hydrogen peroxide/p-iodophenol etc.; for glucose oxidase in colorimetry, glucose/horseradish peroxidase/ABTS (2,2'-azinodi(3-ethylbenzthiazoline)-6-sulfonic acid), or in fluorometry, glucose/horseradish peroxidase/p-hydroxyphenyl propionic acid, or in chemiluminescence, glucose/luminol/Fe(CN)$_6^{3+}$, glucose/TCPO (bis(2,4,6-trichlorophenyl) oxalate)/ANS (8-anilinonaphthalene sulfonic acid, glucose/isoluminol/microperoxidase, glucose/lucigenin/OH—/copper chloride etc.; for β-D-galactosidase in colorimetry, o-nitrophenyl β-D-galactopyranoside, or in fluorometry, 4-methylumbelliferyl β-D-galactoside, or in chemiluminescence, lactose/glucose oxidase/isoluminol/microperoxidase, lactose/glucose oxidase/TCPO (bis(2,4,6-trichlorophenyl) oxalate)/ANS (8-anilinonaphthalene sulfonic acid), AMPGD (3-(4-methoxyspiro(1,2-deoxydioxytane-3,2'-tridecane-4-phenyl), o-NPGal (o-nitro-β-D-galactoside)/GalDH (galactose dehydrogenase)/NAD$^+$/NADH, or in bioluminescence, o-NPGal (o-nitro-β-D-galactoside)/GalDH (galactose dehydrogenase)/NAD$^+$/NADH etc.; for glucose-6-dehydrogenase in an absorbance method, glucose-6-phosphoric acid/NADP$^+$, or in chemiluminescence, glucose-6-phosphoric acid/NAD(P)+/NAD(P)H etc., and the usable substrate may be any substrates for the enzyme used.

After coloration, the sample is measured at a predetermined wavelength as such or after the reaction termination solution is added. For example, for alkali phosphatase, p-nitrophenyl phosphoric acid substrate is measured at 405 nm in colorimetry, 4-methylumbelliferyl phosphoric acid substrate in fluorometry, or AMPPD or CSPD in chemiluminescence; and for peroxidase, 5-aminosalicylic acid substrate at 492 nm in colorimetry, ABTS substrate at 340 nm or 414 nm (oxide) in colorimetry, o-phenylenediamine substrate at 492 nm (pH 1.0) or 445 nm (pH 5.0) in colorimetry, tetramethyl benzidine substrate in colorimetry at 655 nm or at 450 nm (when the reaction is terminated with hydrochloric acid or sulfuric acid), p-hydroxyphenyl propionic acid in fluorometry, or luminol/hydrogen peroxide substrate in chemiluminescence.

After quantification, data processing software commercially available (for example, Delta Soft) or the like is used, and the concentrations of both the samples to which the interfering substance was added and not added are calculated. The determined concentrations are compared in terms of recovery in the presence or absence of the interfering substance as described below, and a sample showing nearly 100% recovery (50 to 200%) even in the presence of the interfering substance at a higher concentration is selected as an antibody having high resistance to the interfering substance. The recovery is calculated according to the following equation:

Recovery (%)=calculated concentration of the substance to be measured/calculated concentration of the added substance to be measured×100

For screening of a hybridoma producing the desired antibody, various methods can be used, but such methods include e.g. an ELISA method wherein a culture supernatant of a hybridoma is added to a microplate onto which carrier protein such as OVA bound to a hapten of the substance to be measured has been adsorbed, and then an anti-mouse immunoglobulin antibody labeled with horseradish peroxidase (abbreviated hereinafter to HRP) is added, and the antibody bound to the solid phase of the plate is detected. The antibody activity-positive hybridoma is immediately subjected to cloning, and usually this can be easily carried out by known limiting dilution or the like.

The antibody titer of a supernatant of the cloned hybridoma is measured in the method described above, and a hybridoma producing an antibody of high titer stably can be selected to give the desired hybridoma producing the monoclonal antibody.

The hybridoma obtained by the method described above includes, e.g., mouse hybridomas EE2-227, E1-420 and E2-73 obtained in Example 1 described later. These have been deposited since Apr. 25, 2001, as Accession Nos. FERM-BP7567, FERM-BP7568 and FERM-BP7569, respectively, with the International Patent Organism Depositary (IPOD), National Institute of Advanced Industrial Science and Technology (AIST) at 1-1, Doshomuchi 4-chome, Chuo-ku, Osaka-shi, Japan.

EXAMPLES

The present invention is described in more detail by reference to the following Examples.

Example 1

1. Preparation of a Monoclonal Antibody 1-1 Preparation of a Hapten (1) Preparation of a Hapten for Ethynylestradiol Antibody 1.0 g of ethynylestradiol (EE2) and 0.76 g of sodium methylate were dissolved in 35 ml of ethanol, and then 0.41 g of monochloroacetic acid was further added to the mixture. The mixture was heated under reflux for 22 hours, concentrated under reduced pressure and partitioned by adding about 100 ml each of water and ethyl acetate. The aqueous layer was washed with 50 ml of ethyl acetate, and was acidified with conc. hydrochloric acid (pH 1–2). The solution was extracted with 100 ml and 50 ml of ethyl acetate, and the organic layer was washed with 30 ml of saturated sodium chloride solution and dehydrated over sodium sulfate anhydride. The solution was concentrated under reduced pressure, and the concentrate was left at −20° C. for 2 days, whereby it was partially crystallized. A part of the crystals was recovered and used as seed crystals. The concentrate was dissolved in a small amount of acetone, and crystals were precipitated by adding hexane and the seed crystals. The recovered crystals were dried under reduced pressure, whereby the desired product EE2-3-carboxymethyl ether (EE2-3CME) was obtained.

(2) Preparation of a Hapten for 17β-Estradiol Antibody 1.0 g of 17β-estradiol (E2) and 0.82 g of sodium methylate were dissolved in 35 ml of ethanol, and 0.45 g of monochloroacetic acid was further added to the mixture. The mixture was heated under reflux for 2 days, concentrated under reduced pressure and partitioned by adding about 300 ml of water and about 200 ml of ethyl acetate. The aqueous layer was washed with 50 ml of ethyl acetate, and the aqueous layer was acidified with conc. hydrochloric acid (pH 1–2). The solution was extracted twice with 100 ml of ethyl acetate, and the organic layer was washed with 30 ml of saturated sodium chloride solution and dehydrated over sodium sulfate anhydride. The solution was concentrated under reduced pressure, and the concentrate was dissolved in a small amount of acetone, and crystals were precipitated by adding isopropyl ether (IPE). The recovered crystals were washed with IPE and dried under reduced pressure, whereby the desired product E2-3-carboxymethyl ether (E2-3CME) was obtained.

(3) Preparation of a Hapten for Estrone Antibody 20 g of estradiol-3,17-diacetate (E2-3,17-diAce) was dissolved in 25 ml of acetic acid, and ⅘ part of a mixture of 9 g of chromic acid anhydride, 27 ml of acetic acid and 4 ml of water was gradually added to the above solution under cooling. The mixture was stirred overnight, then water was added, and the reaction solution was extracted with chloroform, washed with a solution of potassium carbonate, dehydrated over sodium sulfate and concentrated under reduced pressure. The concentrate was dissolved in benzene, subjected to column chromatography (Wako gel 2w) and eluted with hot benzene to separate crude 6-oxo-E2-3,17-diAce (the starting materials were removed under monitoring with TLC). This substance was dissolved in 2-methoxy-ethanol, and an equal volume of 20 % NaOH was added, and the mixture was reacted at 100° C. for 1 hour. The reaction solution was acidified with dilute hydrochloric acid, eluted with ethyl acetate, dehydrated over sodium sulfate, concentrated under reduced pressure, and 6-oxo-E2 was recrystallized from methanol. 300 mg of 6-oxo-E2 was dissolved in 2 ml of ethanol, 50 mg of fine powder of potassium carbonate was added and 50 µl of benzyl bromide was added. The mixture was stirred at 70° C. for 2 hours and the concentrate was recrystallized from methanol to obtain 6-oxo-E2-3-benzyl ether. The 6-oxo-E2-3-benzyl ether was dissolved in methanol, and carboxymethoxyl amine-½ HCl and sodium methoxide (1.2 moles) were dissolved in a small amount of water, and then diluted with methanol and added to the above solution. The mixture was reacted at room temperature for 1 hour, and after ⅔ part of the reaction solution was evaporated, the solution was acidified with water and HCl, extracted with ethyl acetate and dehydrated over sodium sulfate. The product was dissolved in hexane, then purified by column chromatography on silica gel followed by elution with methanol, and recrystallized from methanol. 0.6 g of the recrystallized substance was dissolved in 2 ml of acetone, and half of a mixed solution of 1 g of chromic acid anhydride, 5 ml of acetic acid and 1 ml of water was added, and after the exothermic reaction was finished, the reaction solution was extracted with ethyl acetate and evaporated to dryness to obtain 6-oxo-E1-3-benzyl ether. 400 mg of 6-oxo-E1-3-benzyl ether was dissolved in 5 ml of methanol, and 100 mg of 5% Pd-C was added, and the mixture was stirred while introducing hydrogen. After the reaction for 1 hour, the reaction solution was evaporated to dryness and recrystallized from methanol, whereby the desired product 6-oxo-E1-6 carboxymethyl oxime (E1-6CMO) was obtained.

1-2 Preparation of an Immunogen 0.1 mol of each hapten out of the 3 haptens obtained in the above 1-1, 0.14 mol of water-soluble carbodiimide, and 0.14 mol of N-hydroxysuccinimide were reacted overnight in 2 ml of dimethyl sulfoxide to form an activated ester. Then, 10 mg of keyhole limpet hemocyanin (KLH) was dissolved in 0.13 mol of sodium bicarbonate (NaHCO$_3$) solution, and 200 µl of the activated ester was added and reacted overnight at 4° C. The reaction solution was dialyzed against Dulbecco's phosphate buffer (PBS) to remove unreacted reagents, and frozen and stored as an immunogen.

1-3 Immunization

Each immunogen obtained in the above 1-2 was dissolved at 500 µg/ml in PBS, and added to an equal volume of Freund adjuvant or RIBI adjuvant system. The mixture was sufficiently emulsified and then administered subcutaneously to BALB/C mice (female) in a dose of 100 µg/mouse, and immunization with a booster was conducted at 2-weeks (Freund) or 3-weeks (RIBI) intervals. After the immunization with a booster was conducted 5 to 6 times, a mouse showing the maximum serum antibody titer was intravenously given the same immunogen (50 μg/0.1 ml PBS/mouse) to complete the final immunization.

1-4 Cell fusion

From the mouse subjected to the final immunization in the above 1-3, the spleen was extracted 3 days after the final immunization to prepare spleen cells. Mouse myeloma cells separately cultured and the spleen cells were contacted in the ratio of 1:5 in the presence of polyethyleneglycol with average molecular weight 4000, whereby cell fusion was effected to give fused cells (hybridoma). This hybridoma was suspended in HAT medium, put to each well of a 96-wells microplate and cultured in a $CO_2$ gas incubator (37° C., 5% $CO_2$).

1-5 Screening of the Hybridoma (1) Preparation of an Assay Plate

A goat anti-mouse IgAGM antibody (#55461 produced by ICN/Cappel) was dissolved at 50 μg/ml in PBS, added at 100 μl/well to a microplate and reacted at 4° C. overnight. The microplate was washed twice with 300 μl/well of T-PBS (PBS containing 0.05% Tween 20), and Block Ace (Snow Brand Milk Products Co., Ltd., Tokyo) diluted 4-fold with PBS was added at 200 μl/well to the plate. After the sample was reacted at 4° C. overnight or longer and stored in a refrigerator until use.

(2) Formation of an Antigen-Enzyme Conjugate (Labeled Antigen)

0.1 mol of each hapten out of the 3 haptens obtained in the above 1-1, 0.14 mol of water-soluble carbodiimide, and 0.14 mol of N-hydroxysuccinimide were reacted overnight in 2 ml of dimethyl sulfoxide to form an activated ester. Then, 10 mg of horseradish peroxidase (HRP) was dissolved in 10 ml of 0.13 mol sodium bicarbonate ($NaHCO_3$) solution, and 15 μl of the activated ester was added and reacted overnight at 4° C. Unreacted reagents were removed by ultrafiltration, and the solution was stored at a concentration of 3 mg/ml in a refrigerator.

(3) Primary Screening (Antigen-Binding Ability Test)

100 μl of the culture on a well wherein cell growth had been confirmed in the microplate to which the cells had been put in the above 1-4 was added to the assay plate (after washing twice with 300 μl/well of PBS (or T-PBS) before use) prepared in (1). After the reaction for 1 hour at room temperature, the plate was washed 3 times with 300 μl/well of T-PBS, and the labeled antigen prepared in 1-5 (2) to the antibody against the target substance was diluted at 5000-fold with T-PBS and added to the microplate. After the reaction for 1 hour at room temperature, the plate was washed 3 times with 300 μl/well of T-PBS, and a TMB peroxidase substrate kit (Nippon Bio-Rad Laboratories, Tokyo, #172-1066: hereinafter referred to as "the coloration substrate") was added in a volume of 100 μl/well. After the reaction for 30 minutes at room temperature, the coloration reaction was stopped by adding 100 μl/well of 1 N phosphoric acid. The absorbance at a wavelength of 450 nm was read, and cells showing an absorbance of higher than 1 were then put on a 24-wells microplate for scaled up cultivation.

(4) Secondary Screening (Female Hormone Inhibition Test)

Out of the cells put to a 24-wells microplate in the above 1-5 (3), a culture of cells on a well wherein sufficient cell growth had been confirmed was added to wells in a volume of 100 μl/well in the assay plate (after washing twice with 300 μl/well of PBS (or T-PBS) before use) prepared in (1). After the reaction at room temperature for 1 hour, the plate was washed 3 times with 300 μl/well of T-PBS, and the female hormone as the subject of quantification (1 ng/ml in 10% methanol (MeOH)) or 10% MeOH only (control) and the labeled antigen diluted at 5000-fold with T-PBS to the antibody against the target substance were mixed in equal volumes and added to the microplate. After the reaction at room temperature for 1 hour, the plate was washed 3 times with 300 μl/well of T-PBS, and the coloration substrate was added in a volume of 100 μl/well. After the reaction for 30 minutes at room temperature, the coloration reaction was stopped by adding 100 μl/well of 1 N phosphoric acid. The absorbance was read at a wavelength of 450 nm, and those cells confirmed to reduce the absorbance by 20% or more relative to that of the control in the presence of the female hormone were subjected to cloning in a usual manner, and candidates for hybridomas producing the desired antibody were obtained as shown below.

1-6 Preparation of a Purified Antibody

The cell culture supernatant was fractionated with 45 to 50% saturated ammonium sulfate and then subjected in a usual manner to protein G affinity chromatography, while the mouse ascites fluid was directly subjected to protein G affinity chromatography, to give each purified antibody.

2. Selection of an Antibody Resistant to an Interfering Substance

The culture supernatant obtained in the above 1-5 (4) was used to conduct a test on resistance of each antibody to an interfering substance. As the interfering substance, a surfactant and a humic substance which occur at a high concentration in the environment and can be concentrated together with a substance to be measured in the step of pre-treating the substance to be measured were used.

Experimental Method 1

According to 1-5 (4), the degree of dilution of the culture supernatant, at which the antibody attained the highest sensitivity in quantification of the female hormone, was determined. Then, to an anti-mouse IgG immobilized plate to which the antibody in the supernatant had been bound at that concentration was added 100 μl of a mixture consisting of equal amounts of the following sample and the labeled antigen (diluted 5000-fold with T-PBS) to the antibody against a target substance to be measured. The sample used was a solution containing or not containing the female hormone as the subject of quantification at a concentration of 0.5 μg/L in (0, 10, 100, 1000 mg/L in 10% MeOH) sodium linear-alkylbenzene sulfonate (LAS), alkylphenol ethoxylate (APE) or alkyl ethoxylate (AE) or in (0, 1, 10, 100 mg/L in 10% MeOH) sodium humate. According to the above 1-5 (4), ELISA quantification was conducted, and the concentration of the female hormone in each sample was calculated by comparison with a standard curve prepared by standard solutions of known concentrations. The calculated value was divided by the concentration of the female hormone added (0.5 μ/L) and multiplied by 100 to calculate the recovery.

Results

TABLE 1

| | | | Influencing concentration of the interfering substance | | | |
|---|---|---|---|---|---|---|
| Subject of quantification | Antibody | Presence or absence of the interfering substance during screening | Influencing concentration (ppm) | | | |
| | | | LAS | APE | AE | Sodium humate |
| EE2 | EE2-227 | present | 1000 | 1000 | 1000 | 100 |
| | EE2-8 | absent | 10 | 10 | 10 | 10 |
| E2 | E2-73 | present | 1000 | 100 | >1000 | 100 |
| | E2-CC | absent | 100 | 100 | 100 | 100 |

TABLE 1-continued

Influencing concentration of the interfering substance

| Subject of quantification | Antibody | Presence or absence of the interfering substance during screening | Influencing concentration (ppm) | | | |
|---|---|---|---|---|---|---|
| | | | LAS | APE | AE | Sodium humate |
| | (commercial kit) E2-NG | absent | 100 | 100 | 10 | 100 |
| | (commercial kit) E2-RB | absent | 100 | 10 | 100 | 100 |
| | (commercial kit) | | | | | |
| E1 | E1-420 | present | 1000 | 100 | >1000 | 10 |

Abbreviations of the commercial kits:
E2-CC (Estradiol Enzyme Immunoassay Kit, Cat #582251, Cayman Chemical Company, USA), E2-NG (Estradio ELISA Kit, Product #402110, Neogen Corporation, USA) and E2-RB (RIDASCREEN Estradiol, Cat #04031, R-Biopharm GmbH, Germany)

Out of the anti-EE2 antibodies, the anti-EE2-227 antibody selected in this method showed about 50 to 200% recovery even if the concentration of the interfering substance was about 10 to 100 times as high as that for the anti-EE2-8 antibody (control) obtained without using this selection method, and thus a mouse hybridoma EE2-227 strain (FERM BP-7567) producing the antibody highly resistant to the interfering substance was selected.

Out of the anti-E2 antibodies, the anti-E2-73 antibody selected in this selection method showed 50 to 200% recovery even if the concentration of the interfering substance, the surfactant was about 10 to 100 times as high as that for the 3 antibodies (E2-CC, E2-NG and E2-RB) used in the commercial ELISA kit and obtained without using this selection method, so as a mouse hybridoma producing the antibody highly resistant to the interfering substance, the E2-73 strain (FERM BP-7569) was selected.

Further, the anti-E1-420 antibody selected in this selection method had high resistance to the surfactant, which was comparable with that of the anti-E2-73 antibody, so as a mouse hybridoma producing the anti-E1-420 antibody, the E1-420 strain (FERM-BP-7568) was selected.

Example 2

Preparation of an EE2-ELISA Kit (1) Preparation of an "Immobilized Plate"

A goat anti-mouse IgG antibody (Code No. 55479, ICN/Cappel Ltd.) dissolved in Dulbecco's PBS(−) (Code No. 041-20211, Wako Pure Chemical Industries, Ltd.) was pipetted into an immobilizing plate (Costar, EIA/RIA plate strip 8, #2592) in an amount of 0.5 μg/well, and the plate was left at 4° C. overnight, and then washed 3 times with 300 μl of washing solution (T-PBS). A blocking solution (1% BlocAce by Snow Brand Milk Products Co., Ltd. +0.05% Slaoff 72N (Slamonia 28 N) by Takada Chemical Industries, Ltd. in PBS) was added in a volume of 200 μL/well, and the plate was left at 4° C. overnight, then washed 3 times with 300 μL of washing solution (T-PBS). Then, the ethynylestradiol antibody (EE2-227) dissolved in PBS (containing 0.05% Slaoff 72N +0.1% BSA) was added in an amount of 0.002 μg/well, and the plate was left at 4° C. overnight, and then washed 3 times with 300 μl of washing solution (T-PBS). A blocking solution (1% BlocAce by Snow Brand Milk Products Co., Ltd. +0.05% Slaoff 72N by Takada Chemical Industries, Ltd. in PBS) was added in a volume of 200 μL/well, and the plate was left at 4° C. overnight, and the whole solution was sucked with an aspirator, and the residual solution was removed by tapping. The immobilizing plate was dried, placed in an aluminum bag, degassed by a vacuum dryer, sealed and stored in a refrigerator at 2 to 8° C. (2) Preparation of "EE2 standard stock solution"

(0.1 mg EE2/L in 10% MeOH)

Preparation of Stock Solution 1 (1000 mg EE2/L):

100 mg of an ethynylestradiol standard (content: 100%) (Code No. 055-05011, Wako Pure Chemical Industries, Ltd.) was accurately weighed, placed in a 100 ml measuring flask and adjusted to 100 ml with methanol.

Preparation of Stock Solution 2 (10 mg EE2/L):

Accurately 1 ml of the stock solution 1 was introduced via a constant delivery pipette into a 100 ml measuring flask and adjusted to 100 ml with methanol.

Preparation of a Standard Stock Solution (0.1 mg EE2/L):

Accurately 1 ml of the stock solution 2 was introduced via a constant delivery pipette into a 100 ml measuring flask and adjusted to 100 ml with methanol and distilled water to prepare 10% methanol solution. 4 ml of the standard stock solution was placed in a suitable vessel and stored in a refrigerator at 2 to 8° C.

(3) Preparation of "Antigen-Enzyme Conjugate Solution"

26 mg of water-soluble carbodiimide (WSC for peptide synthesis, Code No. 348-03631, by Wako Pure Chemical Industries, Ltd.) and 16 mg N-hydroxysuccinimide (NHSI for peptide synthesis, Code No. 089-04032, by Wako Pure Chemical Industries, Ltd.) were dissolved in 2 ml of dimethyl sulfoxide (DMSO, special grade, by Wako Pure Chemical Industries, Ltd.). An aliquot thereof, 0.5 ml, and 10 mg of the hapten (EE2-3CME) prepared in Example 1 were dissolved in 1 ml of DMSO and reacted at room temperature overnight. The resultant reaction solution, 13 AL, and 10 mg of peroxidase (POD for EIA, Code No. 814393, Boehringer) previously dissolved in 10 ml of 1.1% NaHCO$_3$ were reacted at 4° C. overnight under stirring, and the resultant reaction solution was filtered through an ultrafiltration membrane having a fractionation molecular weight of 30,000, and then adjusted finally to 30 ml with PBS containing 0.05% Slaoff 72N to give an antigen-enzyme conjugate solution.

200 μl of the solution was pipetted into a suitable vessel, then capped and stored in a refrigerator at 2 to 8° C.

(4) Preparation of "Antigen-Enzyme Conjugate Solution"

500 μL of TWEEN-20 ((Atras Chemical Industries, Inc.): Poly(oxyethylene) sorbitan monolaurate) (for chemical use, Code No. 160-11522, by Wako Pure Chemical Industries, Ltd.) was dissolved in 4.5 ml distilled water to prepare 10% TWEEN-20 ((Atras Chemical Industries, Inc.): Poly(oxyethylene) sorbitan monolaurate) solution. 13.26 g of Na$_2$HPO$_4$.12H$_2$O, 2.02 g of NaH$_2$PO$_4$.2H$_2$O, 14.61 g of NaCl, 10 ml of 10% 20 ((Atra Chemical Industries, Inc.): Poly(oxyethylene) sorbitan monolaurate) solution, and 200 μl of Slaoff 72N were dissolved in 1 L of distilled water, and 8 ml of the solution was pipetted into a suitable vessel, capped and stored in a frigerator at 2 to 8° C.

(5) Preparation of "6-Fold Conc. Washing Solution"

20 ml of TWEEN-20 ((Atras Chemical Industries. Inc.) Poly(oxvethylene) sorbitan monolaurate) was dissolved in 200 ml of distilled water to prepare 10% TWEEN-20 ((Atras Chemical Industries, Inc.): Poly(oxvethylene) sorbitan monolaurate) solution. Twelve bags of Dulbeccot's PBS (−) (for biochemical use, Code No. 041-20211, by Wako Pure Chemical Industries, Ltd.) and 0.3 ml of Slaoff 72N, 30 ml of 10% TWEEN-20 ((Atras Chemical Industries, Inc.): Poly(oxyethylene) sorbitan monolaurate) were dissolved in 1 L of distilled water and pipetted into a suitable vessel, capped and stored in a refrigerator at 2 to 80° C.

(6) Preparation of "Coloration Substrate Solution-A"

13.4 mg of 5,5'-tetramethylbenzidine (TMBZ, for test and research, Code No. 346-04030 1, by Wako Pure Chemical Industries, Ltd.) was dissolved in 1 ml of dimethyl formamide (DMF, special grade, Code No. 045-02916, by Wako Pure Chemical Industries, Ltd.), and then mixed with 100 ml of 0.1 M sodium acetate buffer (pH 5.5) containing 0.1 g/L TWEEN-20 ((Atras Chemical Industries, Inc.): Poly(oxyethylene) sorbitan monolaurate), pipetted into suitable brown vessels in a volume of 10 ml/vessel, capped and stored in a refrigerator at 2 to 8° C.

(7) Preparation of "Coloring Substrate Solution-B"

30% aqueous hydrogen peroxide (Code No. 081-04215, special grade, Wako Pure Chemical Industries, Ltd.) was diluted to 0.1 g/L with distilled water, pipetted into suitable vessels in a volume of 5 ml/vessel, capped and stored in a refrigerator at 2 to 8° C.

(8) Preparation of "Coloration-Stop Solution"

1 N phosphoric acid solution was prepared, pipetted into suitable vessels in a volume of 15 ml/vessel, capped and stored at room temperature.

The kit constituents in (1) to (8) prepared above are packed in a box to complete an EE2-ELISA kit.

Example 3

Quantification by the EE2-ELISA Kit

Quantification Using the EE2-ELISA Kit Prepared in Example 2 was as Follows:

(1) Preparation of "Ethynylestradiol (EE2) Standard Solutions"

The EE2 standard stock solution (0.1 mg/L solution in 10% methanol) was diluted with methanol and distilled water to prepare EE2 standard solutions at necessary concentrations (for example, 0, 0.05, 0.1, 0.3, 1.0, 3.0 µg/L in 10% methanol).

(2) Preparation of "Antigen-Enzyme Complex Solution"

7 mL of the "antigen-enzyme conjugate solution" was added to 14 µL of the "antigen-enzyme conjugate solution" to prepare an "antigen-enzyme conjugate solution".

(3) Preparation of "Mixed Solution"

100 µL/well of a quantification sample or the "EE2 standard solution" (both are 10% methanol solutions) and 100 µL/well of the "antigen-enzyme conjugate solution" were mixed on a "mixing microplate".

(4) Antigen-Antibody Reaction (Competitive Reaction)

The "mixed solution" prepared in (3) was pipetted into the "anti-EE2 monoclonal antibody-immobilized plate" in a volume of 100 µl/well and reacted at room temperature for 60 minutes.

(5) Preparation of "Washing Solution"

During the antigen-antibody reaction, the "6-fold conc. washing solution" and distilled water were mixed in the ratio of 1:5, to prepare a "washing solution".

(6) Removal of Unreacted Materials

The antigen-antibody reaction solution was discarded, and each well was washed 3 times with 300 µL/well of the "washing solution".

(7) Preparation of "Coloration Reagent"

The "coloration substrate solution-A" and "coloration substrate solution-B" were mixed in the ratio of 3:1, to prepare a "coloration reagent".

(8) Coloration Reaction/Stop of the Reaction

The "coloration reagent" prepared in (7) was added in the volume of 100 µL/well, the mixture was reacted at room temperature for 30 minutes, and the "coloration-stop solution" was added in a volume of 100 µL/well to stop the reaction.

(9) Colorimetry and Calculation of the Concentration

The absorbance was measured at a wavelength of 450 nm with a plate reader, and the concentration of EE2 in the sample was determined from a standard curve.

Example 4

Preparation of a Standard Curve by the EE2-ELISA Kit

A standard curve prepared according to Example 3 is shown in FIG. 1. The EE2 concentration was plotted on the ordinate [sic], and the ratio of the absorbance at each EE2 concentration to the absorbance at the concentration of 0 µg/L EE2 (degree of inhibition, B/BO %) was plotted on the abscissa [sic]. From this result, it was estimated that the quantification range of EE2 lay in about 0.05 to 3 µg/L.

Example 5

Cross-Reactivity Test

For the estrogens shown in [Table 2], the respective standard curves were prepared in the same manner as in Example 4, and the EE2 concentration ($IC_{50}$) at which the degree of inhibition was 50% was determined and the cross-reactivity was determined from the following equation, and the results are shown in [Table 2].

Cross-reactivity (%)=$IC_{50}$ of estrogen determined/ $IC_{50}$ of EE2×100

TABLE 2

| Cross-reactivity of EE2-227 antibody | |
|---|---|
| Estrogens | Cross-reactivity (%) |
| Ethynylestradiol (EE2) | 100.0 |
| Estrone (E1) | <0.2 |
| 2-Methoxy E1 | <0.2 |
| 17β-Estradiol (E2) | <0.2 |
| E2-17-glucuronide | <0.2 |
| E2-3-glucuronide | <0.2 |
| E2-3-sulfate-17-glucuronide | <0.2 |
| Estriol (E3) | <0.2 |
| 16-Epi-E3 | <0.2 |
| E3-16-glucuronide | <0.2 |

The anti-EE2-227 antibody had high specificity for EE2, and hardly reacted with other estrogens.

Example 6

Comparison Between LC-MS/MS and ELISA in Quantifications of Waste Water Treatment Process (WWTP) Water 10 L of WWTP water was filtered through a glass fiber filter and adjusted to pH 5 with 1 M acetate buffer (pH 5.0). Then, the water was passed through a C-18 solid phase cartridge previously conditioned with 5 ml methanol and 10 ml distilled water, and then the cartridge was washed with 5 ml each of distilled water and hexane. EE2 was eluted with 5 ml dichloromethane from the C-18 solid phase cartridge, and the eluent was evaporated into dryness in a nitrogen stream (40° C.), then dissolved in 10 % MeOH, and the concentration of EE2 in the sample was quantified according to Example 3.

For ELISA quantification, a commercial ELISA kit for EE2 (#04330, by R-Biopharm GmbH, German) was also used as the control, and quantification was carried out according to the accompanying instructions.

Further, a sample treated in the same manner was also analyzed by LC-MS/MS according to the method of Tsujimura et al. (Memorial Lecture in the 50th anniversary of the founding of Chemicals Evaluation and Research Institute, Japan, and Abstracts of Lectures in the 4th Research Presentation, p.17–26, 1999), and the result was compared with that in ELISA. The results are shown in [Table 3].

TABLE 3

Comparison of quantifications

| Method | Method of acquiring the antibody | Antibody | EE2 concentration (ng/L) | ELISA/LC Ratio |
|---|---|---|---|---|
| ELISA | Method described in this specification | EE2-227 | 0.26 | 1.2 |
| ELISA | Control | Commercial kit | 1.69 | 7.7 |
| LC-MS/MS | | | 0.22 | |

The quantification by the ELISA kit using the EE2-227 antibody obtained and selected as the interfering substance-resistant antibody in this selection method was similar to that by LC-MS/MS, but the quantification by the commercial ELISA kit using an antibody obtained without using this selection method was about 8 times as high as that by LC-MS/MS, and this quantification was considered to be influenced by an interfering substance present in the concentrate.

INDUSTRIAL APPLICABILITY

Even if a test sample containing a target substance to be measured is contaminated with a substance interfering with antigen-antibody reaction, the antibody resistant to a substance interfering with antigen-antibody reaction selected by the method of this invention, is not influenced by the interfering substance and can analyze and measure the target substance, and further it is a useful antibody which can also be used for concentrating the target substance to be measured.

The invention claimed is:

1. A hybridoma producing a monoclonal antibody, which is resistant to a substance interfering with antigen-antibody reaction, wherein the hybridoma is selected from the group consisting of mouse hybridoma EE2-227 (FERM BP-7567), mouse hybridoma E1-420 (FERM BP-7568) and mouse hybridoma E2-73 (FERM BP-7569).

2. A monoclonal antibody, which is resistant to a substance interfering with antigen-antibody reaction, wherein the antibody is produced by a hybridoma selected from the group consisting of mouse hybridoma EE2-227 (FERM BP-7567), mouse hybridoma E1-420 (FERM BP-7568) and mouse hybridoma E2-73 (FERM BP-7569).

3. A kit for immunological analysis of a target substance to be measured, which comprises the monoclonal antibody resistant to a substance interfering with antigen-antibody reaction of claim 2.

4. A kit for immunological concentration of a target substance to be measured, which comprises the monoclonal antibody resistant to a substance interfering with antigen-antibody reaction of claim 2.

* * * * *